United States Patent [19]

Macias

[11] Patent Number: 5,972,988
[45] Date of Patent: Oct. 26, 1999

[54] METHOD FOR TREATMENT OF CHRONIC BRONCHITIS USING INDOLE COMPOUNDS

[75] Inventor: William Louis Macias, Indianapolis, Ind.

[73] Assignee: Eli Lilly and Company, Indianapolis, Ind.

[21] Appl. No.: 09/042,686

[22] Filed: Mar. 12, 1998

Related U.S. Application Data

[60] Provisional application No. 60/042,101, Mar. 26, 1997.

[51] Int. Cl.⁶ .................................................. A61K 31/405
[52] U.S. Cl. .......................... 514/415; 514/418; 514/419
[58] Field of Search ...................................... 514/415, 418, 514/419

[56] References Cited

U.S. PATENT DOCUMENTS 5,654,326  8/1997  Bach et al. ............................... 514/419

*Primary Examiner*—Rebecca Cook
*Attorney, Agent, or Firm*—Roger S. Benjamin

[57] ABSTRACT

A method is disclosed for the treatment of chronic bronchitis by administering to a mammal in need thereof a therapeutically effective amount of a 1H-indole-3-glyoxylamide compound.

8 Claims, No Drawings

METHOD FOR TREATMENT OF CHRONIC BRONCHITIS USING INDOLE COMPOUNDS

CROSS REFERENCE

This application claims the benefit of U.S. Provisional Application No. 60/042101, filed Mar. 26, 1997.

FIELD OF THE INVENTION

This invention relates to the use of 1H-indole-3-glyoxylamide compounds for the treatment of chronic bronchitis.

BACKGROUND OF THE INVENTION

Respiratory diseases represent an increasingly important category of illness. The incidence of such diseases is expected to steadily increase with world industrialization and the rise of atmospheric pollutants. Among respiratory diseases of concern is chronic bronchitis.

In man, the lower conductive airway system begins with the trachea which divides into a series of inverted "Y" air conducting passages. The parts of the system of lower conducting airways in man comprise the two stem bronchi, the smaller bronchi, and the bronchioles. If the trachea is regarded as the starting branch, then the bronchi represent 1 to 3 stage branching and the bronchioles are 4 to 16 stage branching. These airway branches are the site of chronic bronchitis.

Chronic bronchitis is a condition associated with excessive tracheobronchial mucus production sufficient to cause cough with expectoration. The primary structures that experience anatomical change in chronic bronchitis are the conductive airways. Bronchial walls become narrowed by vasodilation, congestion, and mucosal edema. Moreover, chronic bronchitis is associated with hyperplasia and hypertrophy of the mucus-producing glands. Patients with predominant bronchitis are often overweight and cyanotic with a history of cough and sputum production.

Cigarette smoking is highly correlated with chronic bronchitis. The excessive mucus production and chromic cough are prominent symptoms of chronic bronchitis often called, "smoker's cough." Inflammation around the small airways is known as respiratory bronchiolitis and is usually one of the earliest changes that occurs in the lungs of cigarette smokers.

Chronic bronchitis is readily distinguished from bronchial asthma. With asthma the smooth muscle tissue in the walls of the bronchi and bronchioles contracts, causing airway obstruction and an increase in airway resistance. Asthma is an episodic disease. During an asthma attack, the smooth muscles surrounding the small airways of the lungs constrict in response to a particular stimulus. The symptoms of asthma often consist of dyspnea, cough, and wheezing.

A great need remains to develop new methods of treating chronic bronchitis by the use of improved therapeutic agents.

SUMMARY OF THE INVENTION

It has been discovered that 1H-indole-3-glyoxylamide compounds are useful for the treatment and prevention of bronchitis in mammals.

The method of this invention comprising administering to a human having chronic bronchitis a therapeutically effective amount of a 1H-indole-3-glyoxylamide compound.

The method of this invention comprising administering to a human having chronic bronchitis a therapeutically effective amount of a 1H-indole-3-glyoxylamide compound of the formula II;

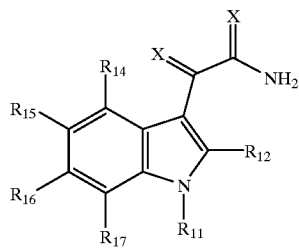

(II)

where X, $R_{11}$, $R_{12}$, $R_{14}$, $R_{15}$, $R_{16}$ and $R_{17}$ are as described infra.

This invention is also a method of reducing the occurrence of excessive tracheobronchial mucus production in a human having chronic bronchitis by administering a therapeutically effective amount of an 1H-indole-3-glyoxylamide compound.

This invention is also a method of reducing the occurrence of inflammation in a human's lower airway conductive system by administering a therapeutically effective amount of an 1H-indole-3-glyoxylamide compound.

This invention is also a method of treating "smoker's cough" in a human by administering a therapeutically effective amount of a 1H-indole-3-glyoxylamide compound.

DETAILED DESCRIPTION OF THE INVENTION

Definitions:

The term "bronchitis" as used herein includes acute bronchitis, chronic bronchitis, acute bronchiolitis and chronic bronchiolitis. Chronic bronchitis is the primary disease state to be treated by the method of this invention.

The term, "therapeutically effective amount" is a quantity of 1H-indole-3-glyoxylamide compound sufficient to significantly alleviate symptoms characteristics of bronchitis in a human in need thereof.

The term, "mammal" includes humans.

The term, "parenteral" means not through the alimentary canal but by some other route such as subcutaneous, intramuscular, intraorbital, intracapsular, intraspinal, intrasternal, or intravenous.

The term, "active compound" means 1H-indole-3-glyoxylamide compounds used in the method of the invention.

The Treatment Method:

Treatment of bronchitis in a human may be therapeutic by administering a 1H-indole-3-glyoxylamide compound to treat an existing condition of bronchitis to mitigate the effects of that event. Alternatively, treatment of bronchitis in a human may be prophylactic by administering a 1H-indole-3-glyoxylamide compound in anticipation of a worsening condition of bronchitis, for example, in a patient whose occupation, lifestyle, or exposure to irritants will expectedly worsen an existing condition of bronchitis.

In general, 1H-indole-3-glyoxylamide compound will be administered to a mammal such as man so that a therapeutically effective amount is received. A therapeutically effective amount may coventionally be determined for an individual patient by administering the active compound in increasing doses and observing the effect on the patient, for example, reduction of coughing and mucus production, spirometer measurements, and etc. Generally, the compound must be administered in a manner and a dose to achieve in the human a blood level concentration of 1H-indole-3-glyoxylamide compound at from 10 to 3000 nanograms/ml, and preferably a concentration of 100 to 800 nanograms/ml.

Methods of Administration.

Administration of the 1H-indole-3-glyoxylamide compound can be by any conventional method. The 1H-indole-3-glyoxylamide compound active ingredient can be administered orally in solid dosage form, such as capsules, tablets, and powders, or in liquid dosage forms, such as elixirs, syrups, and suspensions. It can also be administered parenterally, subcutaneously, intravenously, intramuscularly; by inhalation (e.g., nasal spray—powder or droplets) or topically as an ointment, cream or lotion, on the skin as a transdermal patch; or rectally by suppository.

Generally, the compound will be administered in as a formulation, rather than pure compound. Formulations containing 1H-indole-3-glyoxylamide compounds and methods of making them are described in European Patent Application No. 95302166.4 (EPO Publication No. 0 675 110) and U.S. Pat. No. 5,654,326; the disclosures of which are incorporated herein by reference.

Examples of suitable formulations are those comprising a therapeutically effective amount of 1H-indole-3-glyoxylamide compound together with a pharmaceutically acceptable diluent or carrier, the composition being adapted for the particular route of administration chosen. By "pharmaceutically acceptable" it is meant the carrier, diluent or excipient must be compatible with the 1H-indole-3-glyoxylamide compound in the formulation and not deleterious to the subject being treated. The 1H-indole-3-glyoxylamide compound may be used at a concentration of 0.1 to 99.9 weight percent of the formulation.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved.

For the pharmaceutical formulations any suitable carrier known in the art can be used. In such a formulation, the carrier may be a solid, liquid, or mixture of a solid and a liquid. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. In tablets the 1H-indole-3-glyoxylamide compound is mixed with a carrier having the necessary binding properties in suitable proportions and compacted in the shape and size desired. The powders and tablets preferably contain from about 1 to about 99 weight percent of the 1H-indole-3-glyoxylamide compound.

Sterile liquid form formulations include suspensions, emulsions, syrups and elixirs. The active ingredient can be dissolved or suspended in a pharmaceutically acceptable carrier, such as sterile water, saline, dextrose solution, sterile organic solvent or a mixture of both.

The method of the invention can be practiced using pharmaceutical formulations containing compounds of the invention administered through the skin by an appliance such as a transdermal patch, as described in U.S. Pat. Nos. 5,296,222 and 5,271,940, the disclosures of which are incorporated herein by reference. Lipophilic prodrug derivatives of the compounds for formula II are particularly well suited for transdermal absorption administration and delivery systems.

General Aspects of the Method:

It will be apparent to those skilled in the art that a compound of the present invention can be co-administered with other therapeutic or prophylactic agents and/or medicaments (viz., other medicaments having utility for treating bronchitis) that are not medically incompatible therewith. Examples of other medications for chronic bronchitis are methylxanthines (e.g., ethylene diamine salt of theophylline), sympathomimetics with strong $beta_2$-adrenergic stimulating properties, and anticholinergics.

For patients with acute or chronic bronchitis, the treatment regimen may stretch over many days to months or to years. Oral dosing is preferred for patient convenience and tolerance. With oral dosing, one to four oral doses per day, each from about 0.01 to 25 mg/kg of body weight with preferred doses being from about 0.1 mg/kg to about 1 mg/kg.

Parenteral administration (particularly, intravenous administration) is often preferred in instances where rapid alleviation of patient distress is required. With parenteral administration doses of 0.01 to 100 mg/kg/day administered continuously or intermittently throughout the day may be used. For parenteral administration, the compound may be administered in a physiologic saline vehicle (e.g., 0.9% normal saline, 0.45% normal saline, etc.) a dextrose vehicle (e.g., 5% dextrose in water), or a combination of saline and dextrose vehicle (0.9% normal saline in 5% dextrose). Inhalation therapy also may be useful either alone or as an adjunct to other routes of administration. With inhalation therapy, doses necessary to produce a decrease in mucus production and/or a resolution of the clinical symptoms of acute or chronic bronchitis are readily determined and used.

The specific dose of 1H-indole-3-glyoxylamide compound administered according to this invention to obtain therapeutic or prophylactic effects will, of course, be determined by the particular circumstances surrounding the case, including, for example, the compound administered, the route of administration, the size and age of the patient, the severity of the chronic bronchitis, and the condition being treated.

1H-indole-3-glyoxylamide Compounds Used in the Method of Treating Bronchitis:

The method for treating subjects for the occurrence or prevention of chronic bronchitis comprises administering a therapeutically effective amount of a 1H-indole-3-glyoxylamide compound. Suitable 1H-indole-3-glyoxylamide compounds for the practice of the method of treating and preventing chronic bronchitis as taught herein are described in European Patent Application No. 95302166.4 (EPO Publication No. 0 675 110) and U.S. Pat. No. 5,654,326; the disclosures of which are incorporated herein by reference.

Definitions for 1H-indole-3-glyoxylamide Compounds:

The words, "acid linker" refers to a divalent linking group in the 1H-indole-3-glyoxylamide compounds and is symbolized as, —($L_a$)—. This acid linker group has the function of joining the 4 or 5 position of the indole nucleus to an acidic group in the general relationship:

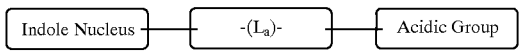

The words, "acid linker length", refer to the number of atoms (excluding hydrogen) in the shortest chain of the linking group —($L_a$)— that connects the 4 or 5 position of the indole nucleus with the acidic group.

Compounds for use in the method of the invention are those having the general formula (II) or a pharmaceutically acceptable salt, solvate or prodrug derivative thereof;

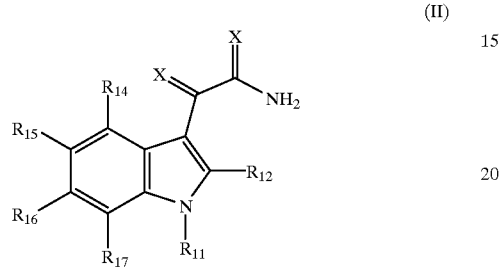

(II)

wherein
each X is independently oxygen or sulfur;
$R_{11}$ is selected from groups (a), (b) and (c) where;
(a) is $C_7$–$C_{20}$ alkyl, $C_7$–$C_{20}$ alkenyl, $C_7$–$C_{20}$ alkynyl; or a carbocyclic radical selected from the group cycloalkyl, cycloalkenyl, phenyl, naphthyl, norbornanyl, bicycloheptadienyl, tolulyl, xylenyl, indenyl, stilbenyl, terphenylyl, diphenylethylenyl, phenyl-cyclohexenyl, acenaphthylenyl, and anthracenyl, biphenyl, bibenzylyl and related bibenzylyl homologues represented by the formula (bb),

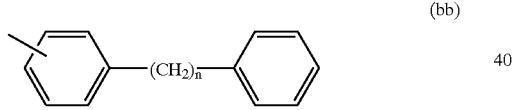

(bb)

where n is a number from 1 to 8; or
(b) is a member of (a) substituted with one or more independently selected non-interfering substituents selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —($CH_2$)$_n$—O—($C_1$–$C_6$ alkyl), benzyloxy, phenoxy, phenylthio, —CHO, amino, amidino, bromo, carbamyl, carboxyl, carbalkoxy, —($CH_2$)$_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8; or (c) is the group —($L_1$)—$R_{81}$; where, —($L_1$)— is a divalent linking group having the formula;

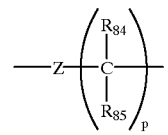

where,
$R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo;
p is 1 to 5,
Z is a bond, —($CH_2$)—, —O—, —N($C_1$–$C_{10}$ alkyl)—, —NH—, or —S—; and
where $R_{81}$ is a group selected from (a) or (b);
$R_{12}$ is hydrogen, halo, $C_1$–$C_3$ alkyl, $C_3$–$C_4$ cycloalkyl, $C_3$–$C_4$ cycloalkenyl, —O—($C_1$–$C_2$ alkyl), or —S—($C_1$–$C_2$ alkyl);
$R_{14}$ is selected from hydrogen, a non-interfering substituent, or the group, —($L_a$)—(acidic group), wherein the acid linker —($L_a$)— has an acid linker length of 2 or 3 atoms and is represented by the formula;

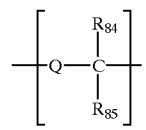

where Q is selected from the group —($CH_2$)—, —O—, —NH—, and —S—; $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, hydroxy, and halo; and the acidic group is selected from -5-tetrazolyl,

—$SO_3H$,

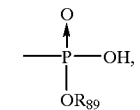

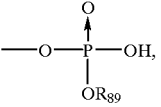

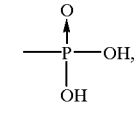

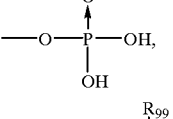

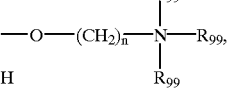

-continued

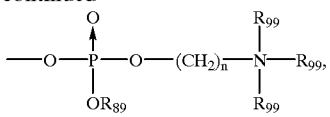

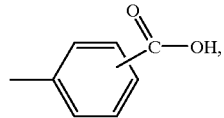

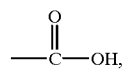

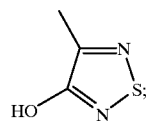

where n is 1 to 8, $R_{89}$ is a metal or $C_1$–$C_{10}$ alkyl, and $R_{99}$ is hydrogen or $C_1$–$C_{10}$ alkyl;

$R_{15}$ is selected from hydrogen, a non-interfering substituent, or the group, —($L_a$)—(acidic group), wherein the acid linker —($L_a$)— has an acid linker length of 3 to 8 atoms and the acid linker group, —($L_a$)— is;

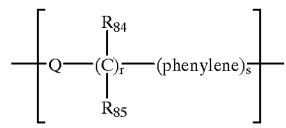

where r is a number from 1 to 7, s is 0 or 1, and Q is selected from the group —(CH$_2$)—, —O—, —NH—, and —S—; and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; and the acidic group is selected from -5-tetrazolyl,

—SO$_3$H,

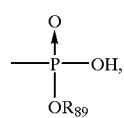

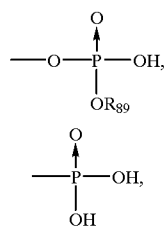

-continued

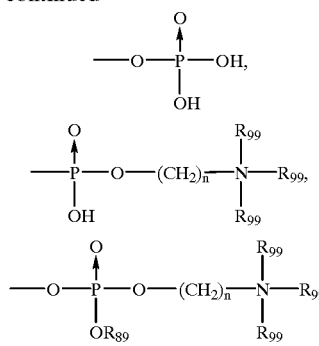

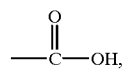

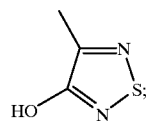

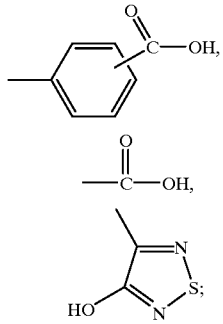

where n is 1 to 8, $R_{89}$ is a metal or $C_1$–$C_{10}$ alkyl, and $R_{99}$ is hydrogen or $C_1$–$C_{10}$ alkyl;

provided that at least one of $R_{14}$ or $R_{15}$ must be the group, —($L_a$)—(acidic group);

$R_{16}$, and $R_{17}$ are each independently selected form hydrogen, non-interfering substituents, selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —(CH$_2$)$_n$—O—($C_1$–$C_6$ alkyl), benzyloxy, phenoxy, phenylthio, —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8.

A preferred class of compounds for the method of the invention are the compounds represented by the formula (II) where both X's are oxygen, only one of $R_{14}$ or $R_{15}$ is —($L_a$)—(acidic group), and the acidic group is carboxyl.

More preferred compounds for use in the method of the invention is a 1H-indole-3-glyoxylamide represented by the formula (I), or a pharmaceutically acceptable salt or ester prodrug derivative thereof;

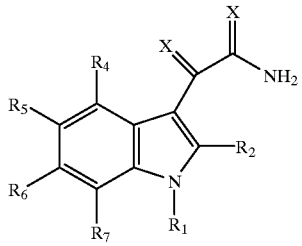
(I)

wherein both X are oxygen;

$R_1$ is selected from the group consisting of

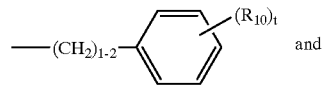
and
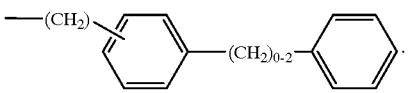

where $R_{10}$ is a radical independently selected from halo, $C_1$–$C_{10}$ alkyl, $C_1$–$C_{10}$ alkoxy, —S—($C_1$–$C_{10}$ alkyl), and $C_1$–$C_{10}$ haloalkyl and t is a number from 0 to 5;

$R_2$ is selected from the group; halo, cyclopropyl, methyl, ethyl, and propyl;

$R_4$ and $R_5$ are independently selected from hydrogen, a non-interfering substituent, or the group, —($L_a$)—(acidic group); wherein —($L_a$)— is an acid linker; provided, the acid linker group, —($L_a$)—, for $R_4$ is selected from the group consisting of;

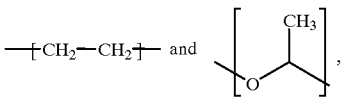

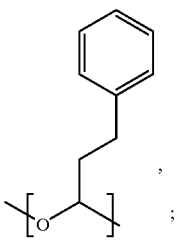

and provided, the acid linker, —($L_a$)—, for $R_5$ is selected from group consisting of;

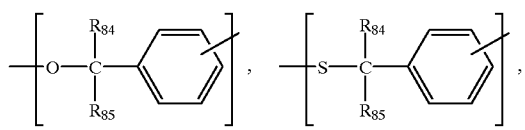

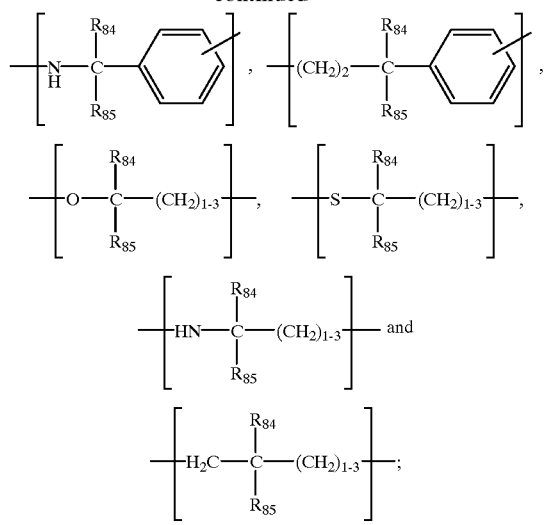

wherein $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; and provided, that at least one of $R_4$ and $R_5$ must be the group, —($L_a$)—(acidic group) and wherein the (acidic group) on the group —($L_a$)—(acidic group) of $R_4$ or $R_5$ is selected from —$CO_2H$, —$SO_3H$, or —$P(O)(OH)_2$;

$R_6$ and $R_7$ are each independently selected form hydrogen and non-interfering substituents, with the non-interfering substituents being selected from the group consisting of the following: $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolulyl, xylenyl, biphenyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(C)O($C_1$–$C_6$ alkyl), —$(CH_2)_n$—O—($C_1$–$C_6$ alkyl), benzyloxy, phenoxy, phenylthio, —($CONHSO_2R$), —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

Specific preferred 1H-indole-3-glyoxylamide compounds and all pharmaceutically acceptable salts, solvates and pro-drug derivatives thereof which are useful in the method of the invention include the following:

(A) [[3-(2-Amino-1,2-dioxoethyl)-2-methyl-1-(phenylmethyl)-1H-indol-4-yl]oxy]acetic acid, (B) dl-2-[[3-(2-Amino-1,2-dioxoethyl)-2-methyl-1-(phenylmethyl)-1H-indol-4-yl]oxy]propanoic acid, (C) [[3-(2-Amino-1,2-dioxoethyl)-1-([1,1'-biphenyl]-2-ylmethyl)-2-methyl-1H-indol-4-yl]oxy]acetic acid, (D) [[3-(2-Amino-1,2-dioxoethyl)-1-([1,1'-biphenyl]-3-ylmethyl)-2-methyl-1H-indol-4-yl]oxy]acetic acid, (E) [[3-(2-Amino-1,2-dioxoethyl)-1-([1,1'-biphenyl]-4-ylmethyl)-2-methyl-1H-indol-4-yl]oxy]acetic acid, (F) [[3-(2-Amino-1,2-dioxoethyl)-1-[(2,6-dichlorophenyl)methyl]-2-methyl-1H-indol-4-yl]oxy] acetic acid (G) [[3-(2-Amino-1,2-dioxoethyl)-1-[4(fluorophenyl) methyl]-2-methyl-1H-indol-4-yl]oxy]acetic acid, (H) [[3-(2-Amino-1,2-dioxoethyl)-2-methyl-1-[(1-naphthalenyl)methyl]-1H-indol-4-yl]oxy]acetic acid, (I) [[3-(2-Amino-1,2-dioxoethyl)-2-ethyl-1-(phenylmethyl)-1H-indol-4-yl]oxy]acetic acid, (J) [[3-(2-Amino-1,2-dioxoethyl)-1-[(3-chlorophenyl) methyl]-2-ethyl-1H-indol-4-yl]oxy]acetic acid, (K) [[3-(2-Amino-1,2-dioxoethyl)-1-([1,1'-biphenyl]-2-ylmethyl)-2-ethyl-1H-indol-4-yl]oxy]acetic acid, (L) [[3-(2-amino-1,2-dioxoethyl)-1-([1,1'-biphenyl]-2-ylmethyl)-2-propyl-1H-indol-4-yl]oxy]acetic acid, (M) [[3-(2-Amino-1,2-dioxoethyl)-2-cyclopropyl-1-(phenylmethyl)-1H-indol-4-yl]oxy]acetic acid, (N) [[3-(2-Amino-1,2-dioxoethyl)-1-([1,1'-biphenyl]-2-ylmethyl)-2-cyclopropyl-1H-indol-4-yl]oxy]acetic acid, (O) 4-[[3-(2-Amino-1,2-dioxoethyl)-2-ethyl-1-(phenylmethyl)-1H-indol-5-yl]oxy]butanoic acid, (P) mixtures of (A) through (P) in any combination.

Preferred specific 1H-indole-3-glyoxylamide compounds for practicing the method of the invention are the following:

(AA) ((3-(2-amino-1,2-dioxoethyl)-1-((1,1'-biphenyl)-3-ylmethyl)-2-methyl-1H-indol-4-yl)oxy)acetic acid isopropyl ester;

(BB) ((3-(2-Amino-1,2-dioxoethyl)-1-((1,1'-biphenyl)-3-ylmethyl)-2-methyl-1H-indol-4-yl)oxy)acetic acid, morpholinylethyl ester; and (CC) ((3-(2-amino-1,2-dioxoethyl)-1-((1,1'-biphenyl)-3-ylmethyl)-2-methyl-1H-indol-4-yl)oxy)acetic acid N,N-diethylglycolamido ester.

Most preferred in the practice of the method of the invention are 1H-indole-3-glyoxylamides selected from the group represented by the formulae:

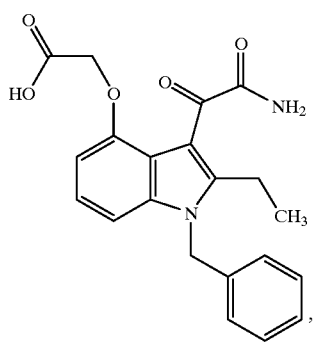
(Va)

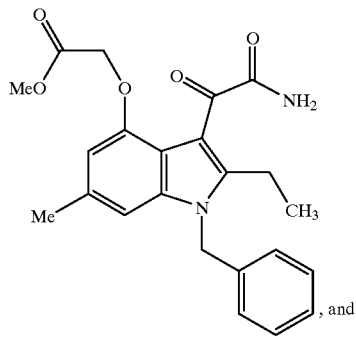
(Vb)

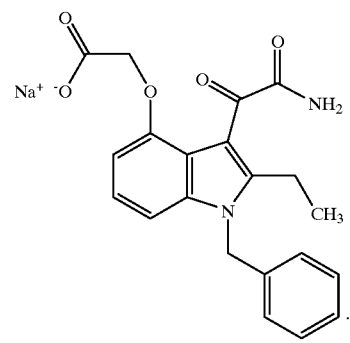
(Vc)

The salts and prodrugs of the 1H-indole-3-glyoxylamide compounds represented by formula (I), (II), the named compounds (A) thru (P), (AA) thru (CC) and the compounds (Va), (Vb), and (Vc), are particularly useful in the method of the invention.

In those instances where the 1H-indole-3-glyoxylamide compounds possess acidic or basic functional groups various salts may be formed which are more water soluble and physiologically suitable than the parent compound. Representative pharmaceutically acceptable salts, include but are not limited to, the alkali and alkaline earth salts such as lithium, sodium, potassium, calcium, magnesium, aluminum and the like. Sodium salts are preferred. Salts are conveniently prepared from the free acid by treating the acid in solution with a base (e.g., NaOH to prepare Na salts) or by exposing the acid to an ion exchange resin.

Included within the definition of pharmaceutically acceptable salts are the relatively non-toxic, inorganic and organic base addition salts of the 1H-indole-3-glyoxylamide compounds used in the method of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," J. Phar. Sci., 66: 1–19 (1977)). Moreover, basic group(s) present in the 1H-indole-3-glyoxylamide compound may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain 1H-indole-3-glyoxylamide compounds may possess one or more chiral centers and may thus exist in optically active forms. Likewise, R- and S- isomers and mixtures thereof, including racemic mixtures as well as mixtures of cis- and trans- isomers, are contemplated for use by the method of this invention.

Prodrugs are derivatives of the 1H-indole-3-glyoxylamide compounds which have chemically or metabolically cleavable groups and become by solvolysis or under physiological conditions the compounds of the invention which are pharmaceutically active in vivo. Derivatives of the 1H-indole-3-glyoxylamide compounds have activity in both their acid and base derivative forms, but the acid derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters (e.g., methyl or ethyl esters) derived from acidic groups (e.g., carboxyl) pendent on the compounds of this invention are preferred prodrugs. Suitable Simple Ester Prodrugs are Represented by the Formula:

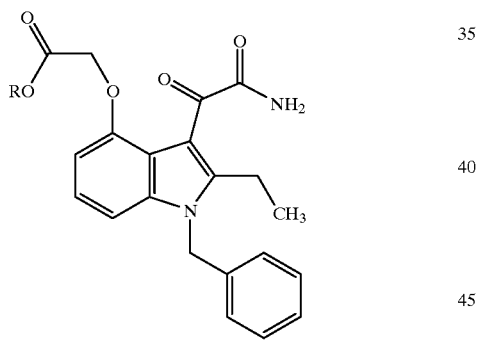

where R is $C_1$–$C_5$ alkyl.

where R is $C_1$–$C_5$ alkyl

In some cases it is desirable to prepare double ester type prodrugs such as (acyloxy) alkyl esters or ((alkoxycarbonyl)oxy)alkyl esters.

The synthesis of the 1H-indole-3-glyoxylamide compounds used in the method of treating chronic bronchitis may be accomplished as described European Patent Application No. 95302166.4, Publication No. 0 675 110 (publ., Oct. 4, 1995). Such synthesis methods also include well-known methods as recorded in the chemical literature and the procedure illustrated in the following preparative reaction scheme:

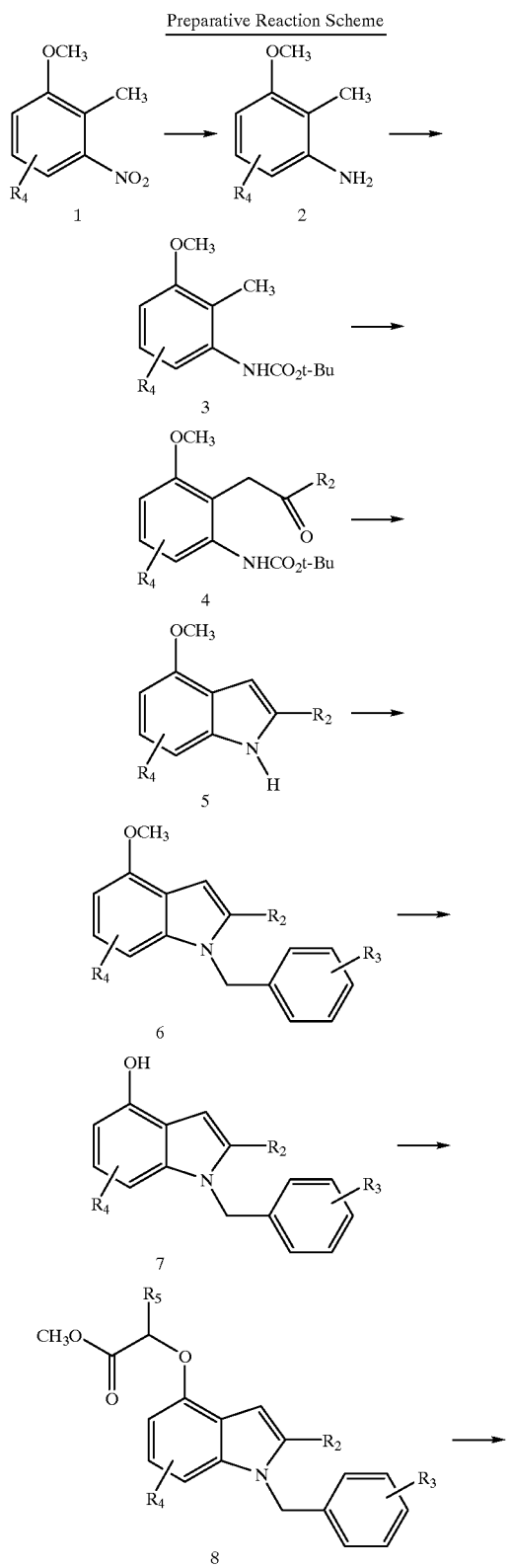

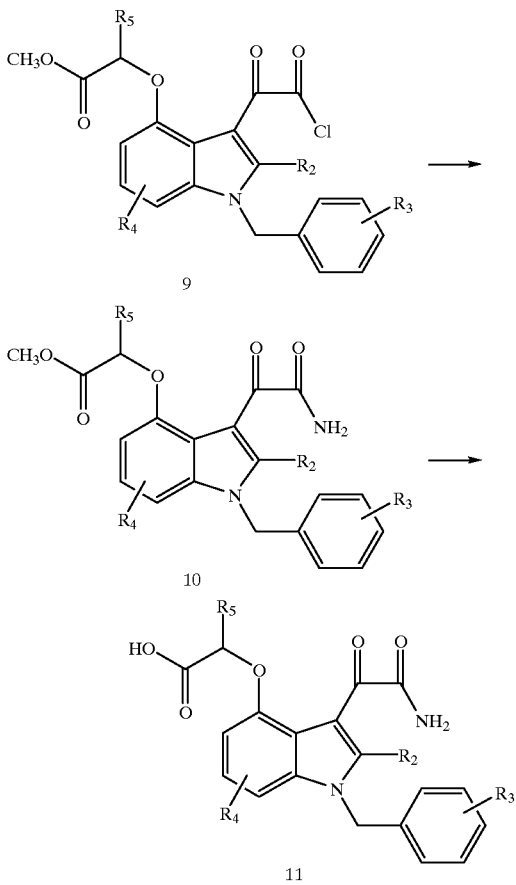

9

10

11

Explanation of Preparative Reaction Scheme:

To obtain the glyoxylamides substituted in the 4-position with an acidic function through an oxygen atom, the reactions outlined in scheme 1 are used (for conversions 1 through 5, see ref. Robin D. Clark, Joseph M. Muchowski, Lawrence E. Fisher, Lee A. Flippin, David B. Repke, Michel Souchet, Synthesis, 1991, 871–878, the disclosures of which are incorporated herein by reference). The ortho-nitrotoluene, 1, is readily reduced to the 2-methylaniline, 2, using Pd/C as catalyst. The reduction can be carried out in ethanol or tetrahydrofuran (THF) or a combination of both, using a low pressure of hydrogen. The aniline, 2, on heating with di-tert-butyl dicarbonate in THF at reflux temperature is converted to the N-tert-butylcarbonyl derivative, 3, in good yield. The dilithium salt of the dianion of 3 is generated at −40 to −20° C. in THF using sec-butyl lithium and reacted with the appropriately substituted N-methoxy-N-methylalkanamide. This product, 4, may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, Adv. Drug Res., 1977, 12, 176, the disclosure of which is incorporated herein by reference). The 4-hydroxyindole, 7, is alkylated with an alpha bromoalkanoic acid ester in dimethylformamide (DMF) using sodium hydride as a base, with reactions conditions similar to that described for the conversion of 5 to 6. The α-[(indol-4-yl)oxy]alkanoic acid ester, 8, is reacted with oxalyl chloride in methylene chloride to give 9, which is not purified but reacted directly with ammonia to give the glyoxamide 10. This product is hydrolyzed using 1N sodium hydroxide in MeOH. The final glyoxylamide, 11, is isolated either as the free carboxylic acid or as its sodium salt or in both forms.

EXAMPLE 1

This Example 1 illustrates the preparation of [[3-(2-Amino-1,2-dioxoethyl)-2-ethyl-1-(phenylmethyl)-1H-indol-4-yl]oxy]acetic acid (as well as its sodium salt and methyl ester)useful in the practice of the method of the invention:

Preparation of [[3-(2-Amino-1,2-dioxoethyl)-2-ethyl-1-(phenylmethyl)-1H-indol-4-yl]oxy]acetic acid, a compound represented by the formula:

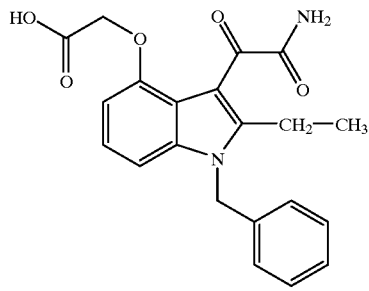

Part A. Preparation of 2-Ethyl-4-methoxy-1H-indole.

A solution of 140 mL (0.18 mol) of 1.3M sec-butyl lithium in cyclohexane was added slowly to N-tert-butoxycarbonyl-3-methoxy-2-methylaniline (21.3 g, 0.09 mol) in 250 mL of THF keeping the temperature below −40° C. with a dry ice-ethanol bath. The bath was removed and the temperature allowed to rise to 0° C. and then the bath replaced. After the temperature had cooled to −60° C., 18.5 g (0.18 mol) of N-methoxy-N-methylpropanamide in an equal volume of THF was added dropwise. The reaction mixture was stirred 5 minutes, the cooling bath removed and stirred an additional 18 hours. It was then poured into a mixture of 300 mL of ether and 400 mL of 0.5N HCl. The organic layer was separated, washed with water, brine, dried over $MgSO_4$, and concentrated at reduced pressure to give 25.5 g of a crude of 1-[2-(tert-butoxycarbonyl)amino)-6-methoxyphenyl]-2-butanone. This material was dissolved in 250 mL of methylene chloride and 50 mL of trifluoroacetic acid and stirred for a total of 17 hours. The mixture was concentrated at reduced pressure and ethyl acetate and water added to the remaining oil. The ethyl acetate was separated, washed with brine, dried ($MgSO_4$) and concentrated. The residue was chromatographed three times on silica eluting with 20% EtOAc/hexane to give 13.9 g of 2-ethyl-4-methoxy-1H-indole.

Analyses for $C_{11}H_{13}NO$: Calculated: C, 75.40; H, 7.48; N, 7.99; Found: C, 74.41; H, 7.64; N, 7.97.

Part B. Preparation of 2-Ethyl-4-methoxy-1-(phenylmethyl)-1H-indole.

2-Ethyl-4-methoxy-1H-indole (4.2 g, 24 mmol) was dissolved in 30 mL of DMF and 960 mg (24 mmol) of 60% NaH/mineral oil was added. After 1.5 hours, 2.9 mL(24 mmol) of benzyl bromide was added. After 4 hours, the mixture was diluted with water and extracted twice with ethyl acetate. The combined ethyl acetate was washed with brine, dried (MgSO$_4$) and concentrated at reduced pressure. The residue was chromatographed on silica gel and eluted with 20% EtOAc/hexane to give 3.1 g (49% yield) of 2-ethyl-4-methoxy-1-(phenylmethyl)-1H-indole.

Part C. Preparation of 2-Ethyl-4-hydroxy-1-(phenylmethyl)-1H-indole.

By the method used in Example 1, Part D, 3.1 g (11.7 mmol) of 2-ethyl-4-methoxy-1-(phenylmethyl)-1H-indole was O-demethylated by treating it with 48.6 mL of 1M BBr$_3$/CH$_2$Cl$_2$ to give a material that was chromatographed on silica gel (eluted with 20% EtOAc/hexane) to give 1.58 g (54% yield) of 2-ethyl-4-hydroxy-1-(phenylmethyl)-1H-indole, mp, 86–90° C.

Analyses for C$_{17}$H$_{17}$NO: Calculated: C, 81.24; H, 6.82; N, 5.57; Found: C, 81.08; H, 6.92; N, 5.41.

Part D. Preparation of [[2-Ethyl-1-(phenylmethyl)-1H-indol-4-yl]oxy]acetic acid methyl ester.

Using the procedure described in Example 1, Part E, 2-ethyl-4-hydroxy-1-(phenylmethyl)-1H-indole (1.56 g, 6.2 mmol) was treated with 248 mg (6.2 mmol) of 60% NaH/mineral oil and then 0.6 mL(6.2 mmol) of methyl bromoacetate. The product was purified by chromatography over silica gel eluting with 20% EtOAc/hexane, to give 1.37 g (69% yield) of [[2-ethyl-1-(phenylmethyl)-1H-indol-4-yl]oxy]acetic acid methyl ester, 89–92° C.

Analyses for C$_{20}$H$_{21}$NO$_3$: Calculated: C, 74.28; H, 6.55; N, 4.33; Found: C, 74.03; H, 6.49; N, 4.60.

Part E. Preparation of [[3-(2-Amino-1,2-dioxoethyl)-2-ethyl-1-(phenylmethyl)-1H-indol-4-yl]oxy]acetic acid methyl ester.

Using the procedure in Example 1, Part F, 1.36 g (4.2 mmol) of [[2-ethyl-1-(phenylmethyl)-1H-indol-4-yl]oxy] acetic acid methyl ester was reacted first with 0.4 mL (4.2 mmol) of oxalyl chloride and then excess ammonia to give a white solid. This was stirred with ethyl acetate and the insoluble material separated and dried to give 1.37 g of a mixture of [[3-(2-amino-1,2-dioxoethyl)-2-ethyl-1-(phenylmethyl)-1H-indol-4-yl]oxy]acetic acid methyl ester and ammonium chloride. This mixture melted at 172–187° C.

Part F. Preparation of [[3-(2-Amino-1,2-dioxoethyl)-2-ethyl-1-(phenylmethyl)-1H-indol-4-yl]oxy]acetic acid.

A mixture of 788 mg (2 mmol) of [3-(2-amino-1,2-dioxoethyl)-2-ethyl-1-(phenylmethyl)-1H-indol-4-yl]oxy] acetic acid methyl ester, 10 mL of in NaOH and 30 mL of MeOH was heated to maintain reflux for 0.5 hour, stirred at room temperature for 0.5 hour and concentrated at reduced pressure. The residue was taken up in ethyl acetate and water, the aqueous layer separated and made acidic to pH 2–3 with 1N HCl. The precipitate was filtered and washed with ethyl acetate to give 559 mg (74% yield) of [[3-(2-amino-1,2-dioxoethyl)-2-ethyl-1-(phenylmethyl)-1H-indol-4-yl]oxy]acetic acid, mp, 230–234° C.

Analyses for C$_{21}$H$_{20}$N$_2$O$_5$: Calculated: C, 65.96; H, 5.80; N, 7.33; Found: C, 66.95; H, 5.55; N, 6.99.

Synthesis of Selected Prodrug 1H-indole-3-glyoxylamide Compounds Useful in the Practice of the Invention:

The synthesis of ((3-(2-amino-1,2-dioxoethyl)-1-((1,1'-biphenyl)-3-ylmethyl)-2-methyl-1H-indol-4-yl)oxy)acetic acid isopropyl ester (compound of formula I, supra.) uses as starting material ((3-(2-amino-1,2-dioxoethyl)-1-((1,1'-biphenyl)-3-ylmethyl)-2-methyl-1H-indol-4-yl)oxy)acetic acid, or a salt thereof (compound of formula II, supra.). This starting material may be prepared by the reaction schemes or method of Example 4 of U.S. Pat. No. 5,654,326 (the disclosure of which is incorporated herein by reference). Similar methods are shown in European Patent Application No. 95302166.4, Publication No. 0 675 110 (publ., Oct. 4, 1995). Other methods well known and recorded in the chemical literature may also be used for preparing the starting material. Procedures useful for the synthesis of the starting material are shown Example 1A set out below:

EXAMPLE 1A

Method of Preparing ((3-(2-amino-1,2-dioxoethyl)-1-((1, 1'-biphenyl)-3-ylmethyl)-2-methyl-1H-indol-4-yl)oxy) acetic acid.

Part A. Preparation of 1-((1,1'-biphenyl)-3-ylmethyl)-2-methyl-4-methoxy-1H-indole.

805 mg (5 mmol) of 4-methoxy-2-methyl-1H-indole is reacted with 200 mg (5 mmol) of 60% NaH/mineral oil (washing with hexane before adding DMF) in 15 mL of DMF and after stirring for 0.5 hour, 1.0 g (5 mmol) of 3-(chloromethyl)biphenyl is added. The mixture is stirred at room temperature for 18 hours, diluted with water and extracted with ethyl acetate. The ethyl acetate solution is washed with brine, dried (MgSO$_4$) and after concentrating at reduced pressure, the residue is chromatographed on silica gel eluting with 20% EtOAc/hexane to give 1.25 g (76% yield) of 1-((1,1'-biphenyl)-3-ylmethyl)-2-methyl-4-methoxy-1H-indole mp, 127°–131° C.

Part B. Preparation of 1-((1,1'-biphenyl)-3-ylmethyl)-2-methyl-4-hydroxy-1H-indole.

A solution of 125 mg (3.8 mmol) of 1-((1,1'-biphenyl)-3-ylmethyl)-2-methyl-4-methoxy-1H-indole is O-demethylated by treating it with 15 mL of 1M BBr$_3$/CH$_2$Cl$_2$. The reaction mixture is stirred at room temperature for 5 hours and concentrated at reduced pressure. The crude product is chromatographed on silica gel and is eluted with 20% EtOAc/hexane to give 1030 mg (87% yield) of 1-((1, 1'-biphenyl)-3-ylmethyl)-2-methyl-4-hydroxy-1H-indole.

Part C. Preparation of ((1-((1,1'-biphenyl)-3-ylmethyl)-2-methyl-1H-indol-4-yl)oxy)acetic acid methyl ester.

1-((1,1'-Biphenyl)-3-ylmethyl)-4-hydroxy-2-methyl-1H-indole (1030 mg, 3.3 mmol) is alkylated by treating with 0.31 mL (3.3 mmol) of methyl bromoacetate and 132 mg (3.3 mmol) and 132 mg (3.3 mmol) of 60% NaH/mineral oil in DMF and stirring maintained for about 17 hours. The mixture is diluted with water and extracted with ethyl acetate. The ethyl acetate solution is washed with brine, dried (MgSO$_4$), and concentrated at reduced pressure. The product is purified by chromatography over silica gel eluting with 20% EtOAc/hexane, to give 1000 mg (79% yield) of ((1-((1,1'-biphenyl)-3-ylmethyl)-2-methyl-1H-indol-4-yl) oxy)acetic acid methyl ester; mp 99°–102° C.

Part D. Preparation of ((3-(2-amino-1,2-dioxoethyl)-1-((1,1'-biphenyl)-3-ylmethyl)-2-methyl-1H-indol-4-yl)oxy) acetic acid methyl ester.

Oxalyl chloride (0.23 mL, 2.6 mmol) is added to 1000 mg (2.6 mmol) of ((1-((1,1'-biphenyl)-3-ylmethyl)-2-methyl-1H-indol-4-yl)oxy)acetic acid methyl ester in 15 mL of methylene chloride and the mixture is stirred for 1.3 hours at room temperature. The mixture is concentrated at reduced pressure, the residue redissolved in 15 mL of methylene chloride, ammonia bubbled in for 0.25 hours, stirred for 0.25 hours and concentrated. The residue is stirred with EtOAc/water and the undissolved material filtered to give 300 mg of ((3-(2-amino-1,2-dioxoethyl)-1-((1,1'-biphenyl)-3-ylmethyl)-2-methyl-1H-indol-4-yl)oxy)acetic acid methyl ester. The residue was chromatographed on silica gel eluting with EtOAc to give an additional 671 mg of product, mp, 175°–179° C. The total combined yield of product was 82%.

Part E. Preparation of ((3-(2-amino-1,2-dioxoethyl)-1-((1,1'-biphenyl)-3-ylmethyl)-2-methyl-1H-indol-4-yl)oxy)acetic acid.

A mixture of 956 mg (2.1 mmol) of ((3-(2-amino-1,2-dioxoethyl)-1-((1,1'-biphenyl)-3-ylmethyl)-2-methyl-1H-indol-4-yl)oxy)acetic acid methyl ester is hydrolyzed at reflux in 10 mL of 1N NaOH and 20 mL of MeOH to give 403 mg (41% yield) of ((3-(2-amino-1,2-dioxoethyl)-1-((1,1'-biphenyl)-3-ylmethyl)-2-methyl-1H-indol-4-yl)oxy)acetic acid, sodium salt, mp, greater than 265° C.

Analyses for $C_{26}H_{21}N_2O_5Na$: Calculated: C, 67.24; H, 4.56; N, 6.03; Found: C, 67.20; H, 4.58; N, 6.03.

There is also obtained 346 mg (37% yield) of ((3-(2-amino-1,2-dioxoethyl)-1-((1,1'-biphenyl)-3-ylmethyl)-2-methyl-1H-indol-4-yl)oxy)acetic acid, mp, 236°–238° C.

Analyses for $C_{26}H_{22}N_2O_5$: Calculated: C, 70.58; H, 5.01; N, 6.33; Found: C, 70.58; H, 5.25; N, 6.11.

Beginning with the indole starting prepared by Example 1A the ((3-(2-amino-1,2-dioxoethyl)-1-((1,1'-biphenyl)-3-ylmethyl)-2-methyl-1H-indol-4-yl)oxy)acetic acid, isopropyl ester compound of the invention is prepared by esterification of the acid or salt form of the starting material. Any ester forming method which is conventional in the chemical arts may be used. A suitable procedure used to prepare the compound of the invention is as described in Example 1B as follows:

EXAMPLE 1B

Preparation of ((3-(2-amino-1,2-dioxoethyl)-1-((1,1'-biphenyl)-3-ylmethyl)-2-methyl-1H-indol-4-yl)oxy)acetic acid isopropyl ester.

In a flask containing 15 ml of dimethylformamide was added with stirring 0.11 ml of 2-bromopropane and 500 mg. of ((3-(2-amino-1,2-dioxoethyl)-1-((1,1'-biphenyl)-3-ylmethyl)-2-methyl-1H-indol-4-yl)oxy)acetic acid, sodium salt. The reaction mixture was stirred at room temperature overnight. The reaction was incomplete. Thereafter, 180 mg of KI was added and the mixture was heated. After 24 hours the reaction mixture was poured into 50 ml of saturated $NaHCO_3$ and extracted with ethyl acetate. The EtOAc solution was washed with water, dried over $Na_2SO_4$, and concentrated at reduced pressure. The title compound was then crystallized from EtOAc/hexane.

Molecular Formula: $C_{29}H_{28}N_2O_5$ Calculated % C=71.89 H=5.83 N=5.78; Found % C=71.77 H=5.70 N=5.84

EXAMPLE 1C

Preparation of ((3-(2-amino-1,2-dioxoethyl)-1-((1,1'-biphenyl)-3-ylmethyl)-2-methyl-1H-indol-4-yl)oxy)acetic acid, morpholino-N-ethyl ester.

In a flask containing 10 ml of dimethylformamide was added with stirring 133 mg. of 4-(2-chloroethyl)morpholine hydrochloride (available from Aldrich Chemical Co., Milwaukee, Wis. USA, Item No. C4, 220-3) and 231 mg. of $CsCO_3$ and 300 mg. of ((3-(2-amino-1,2-dioxoethyl)-1-((1,1'-biphenyl)-3-ylmethyl)-2-methyl-1H-indol-4-yl)oxy)acetic acid, sodium salt. The slurry was heated to 60° C. until a solution formed. Heating was continued overnight until reaction was complete. 20 ml of $H_2O$ was added to the flask and the organic soluble phase extracted with three 20 ml. portions of ethyl acetate. The ethyl acetate solution was washed with water and dried over and dried over $Na_2SO_4$. Removal of solvent gave product verified by IR and NMR to be the title compound.

Molecular Formula: $C_{32}H_{22}N_3O_6$ Calculated % C=69.17 H=5.99 N=7.56; Found % C=69.23 H=5.84 N=7.27

EXAMPLE 1D

Preparation of ((3-(2-amino-1,2-dioxoethyl)-1-((1,1'-biphenyl)-3-ylmethyl)-2-methyl-1H-indol-4-yl)oxy)acetic acid N,N-diethylglycolamido ester.

In a flask containing 10 ml of dimethylformamide was added with stirring 0.1 ml of 2-chloro-N,N-diethylacetamide (available from Aldrich Chemical Co., Milwaukee, Wis. USA; Item No. 25, 099-6) and 300 mg. of ((3-(2-amino-1,2-dioxoethyl)-1-((1,1'-biphenyl)-3-ylmethyl)-2-methyl-1H-indol-4-yl)oxy)acetic acid, sodium salt. The slurry was heated to 60° C. until a solution formed. Heating was continued overnight until reaction was complete. The following morning the reaction mixture was poured into 50 ml of saturated $NaHCO_3$, then extracted with ethyl acetate. The ethyl acetate solution was washed with water, dried over $Na_2SO_4$ and concentrated at reduced pressure. The title compound is crystallized from EtOAc/hexane.

Molecular Formula: $C_{32}H_{33}N_3O_6$ Calculated % C=69.17 H=6.51 N=7.56; Found % C=68.73 H=5.88 N=7.40

EXAMPLE 2

This Example illustrates the practice and efficacy of the method of the invention.

A male volunteer subject, also a chronic cigarette smoker, was a participant in a seven day Phase I pharmacokinetic study. The indole compound, [[3-(2-Amino-1,2-dioxoethyl)-2-ethyl-1-(phenylmethyl)-1H-indol-4-yl]oxy]acetic acid, sodium salt, was administered to the subject as a continuous intravenous infusion for 7 consecutive days. The concentration of active compound in the subject's blood was determined to be approximately 400 nanograms/milliliter. Lung parameters were measured by standard spirometer apparatus.

On the second day after dosage the male subject reported his chronic "smoker's cough" significantly alleviated, breathing improved, coughing and mucus reduced, and tolerance to exercise increased. This alleviation continued during the course of the study and stopped approximately one day after administration of the indole compound was discontinued. This reported improvement during dosing was verified by PEFR spirometer measurements taken during and after the study as set out in Table 1 below:

TABLE 1

| Day | Comp. Dose | FVC (1) | $FEV_1$ (1) | MMEF (1/s) | PEFR (1/s) |
|---|---|---|---|---|---|
| 4 | + | 4.49 | 3.64 | 3.47 | 11.2 |
| 8 | − | 4.33 | 3.53 | 3.55 | 8.06 |

TABLE 1-continued

| Day | Comp. Dose | FVC (1) | FEV$_1$ (1) | MMEF (1/s) | PEFR (1/s) |
|---|---|---|---|---|---|
| 21 | – | 4.00 | 3.56 | 4.20 | 8.88 |

FVC - forced vital capacity
FEV$_1$ - forced expiratory volume (1 minute)
MMEF - maximum mid-expiratory flow
PERF - peak expiratory flow rate
Comp. Dose - (+) active compound given on numbered days 1 to 7
(−) active compound not given after day 7
l - liters. l/s - liters per second.

Thus, during administration of indole compound PEFR rose to 11.2 liters/second, confirming the breathing improvement reported by the subject. After stopping administration of indole compound the PEFR decreased to 8.06–8.88 liters per second, confirming the subject's report that his "smoker's cough" had returned.

While the present invention has been illustrated above by certain specific embodiments, it is not intended that these examples should limit the scope of the invention as described in the appended claims.

I claim:

1. A method for treatment of a human currently afflicted with chronic bronchitis or previously afflicted with chronic bronchitis, said method comprising administering to said human a therapeutically effective amount of a 1H-indole-3-glyoxylamide compound represented by the formula (I) or a pharmaceutically acceptable salt, solvate, or prodrug derivative thereof;

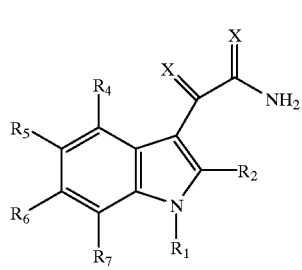

(I)

wherein;
both X are oxygen;
R$_1$ is selected from the group consisting of

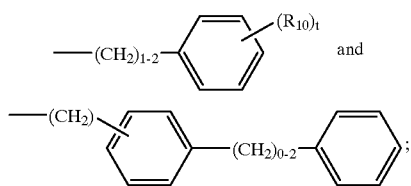

where R$_{10}$ is a radical independently selected from halo, C$_1$–C$_{10}$ alkyl, C$_1$–C$_{10}$ alkoxy, —S—(C$_1$–C$_{10}$ alkyl), and C$_1$–C$_{10}$ haloalkyl and t is a number from 0 to 5;
R$_2$ is selected from the group; halo, cyclopropyl, methyl, ethyl, and propyl;
R$_4$ and R$_5$ are independently selected from hydrogen or the group, —(L$_a$)—(acidic group); wherein —(L$_a$)— is an acid linker; provided, the acid linker group, —(L$_a$)—, for R$_4$ is selected from the group consisting of;

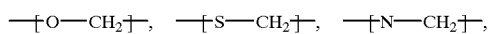

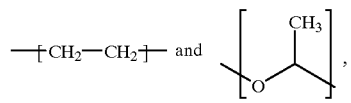

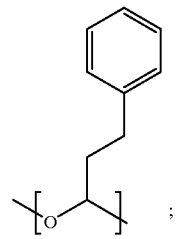

and provided, the acid linker, —(L$_a$)—, for R$_5$ is selected from group consisting of;

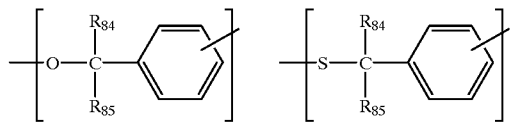

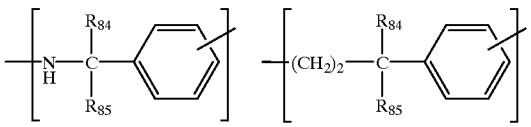

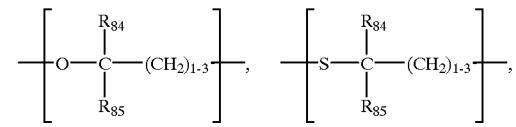

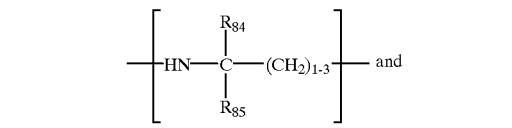

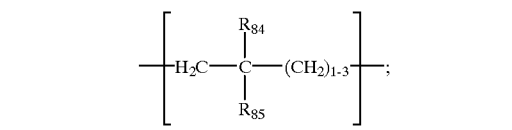

wherein R$_{84}$ and R$_{85}$ are each independently selected from hydrogen or C$_1$–C$_{10}$ alkyl; and
provided, that at least one of R$_4$ and R$_5$ must be the group, —(L$_a$)—(acidic group) and wherein the (acidic group) on the group —(L$_a$)—(acidic group) of R$_4$ or R$_5$ is selected from —CO$_2$H, —SO$_3$H, or —P(O)(OH)$_2$;
R$_6$ and R$_7$ are each independently selected from hydrogen or C$_1$–C$_6$ alkyl.

2. A method for treatment of a human currently afflicted with a chronic bronchitis or previously afflicted with a chronic bronchitis, said method comprising administering to said human in need of such treatment, a therapeutically effective amount of a 1H-indole-3-glyoxylamide compound or a pharmaceutically acceptable salt, solvate, or a prodrug derivative thereof selected from the group consisting of compounds (A) through (P):

(A) [[3-(2-Amino-1,2-dioxoethyl)-2-methyl-1-(phenylmethyl)-1H-indol-4-yl]oxy]acetic acid, (B) dl-2-[[3-(2-Amino-1,2-dioxoethyl)-2-methyl-1-(phenylmethyl)-1H-indol-4-yl]oxy]propanoic acid, (C) [[3-(2-Amino-1,2-dioxoethyl)-1-([1,1'-biphenyl]-2-ylmethyl)-2-methyl-1H-indol-4-yl]oxy]acetic acid, (D) [[3-(2-Amino-1,2-dioxoethyl)-1-([1,1'-biphenyl]-3-ylmethyl)-2-methyl-1H-indol-4-yl]oxy]acetic acid, (E) [[3-(2-Amino-1,2-dioxoethyl)-1-([1,1'-biphenyl]-4-ylmethyl)-2-methyl-1H-indol-4-yl]oxy]acetic acid, (F) [[3-(2-Amino-1,2-dioxoethyl)-1-[(2,6-dichlorophenyl)methyl]-2-methyl-1H-indol-4-yl]oxy]acetic acid;

(G) [[3-(2-Amino-1,2-dioxoethyl)-1-[4(-fluorophenyl)methyl]-2-methyl-1H-indol-4-yl]oxy]acetic acid, (H) [[3-(2-Amino-1,2-dioxoethyl)-2-methyl-1-[(1-naphthalenyl)methyl]-1H-indol-4-yl]oxy]acetic acid, (I) [[3-(2-Amino-1,2-dioxoethyl)-2-ethyl-1-(phenylmethyl)-1H-indol-4-yl]oxy]acetic acid, (J) [[3-(2-Amino-1,2-dioxoethyl)-1-[(3-chlorophenyl)methyl]-2-ethyl-1H-indol-4-yl]oxy]acetic acid, (K) [[3-(2-Amino-1,2-dioxoethyl)-1-([1,1'-biphenyl]-2-ylmethyl)-2-ethyl-1H-indol-4-yl]oxy]acetic acid, (L) [[3-(2-amino-1,2-dioxoethyl)-1-([1,1'-biphenyl]-2-ylmethyl)-2-propyl-1H-indol-4-yl]oxy]acetic acid, (M) [[3-(2-Amino-1,2-dioxoethyl)-2-cyclopropyl-1-(phenylmethyl)-1H-indol-4-yl]oxy]acetic acid, (N) [[3-(2-Amino-1,2-dioxoethyl)-1-([1,1'-biphenyl]-2-ylmethyl)-2-cyclopropyl-1H-indol-4-yl]oxy]acetic acid, and (O) 4-[[3-(2-Amino-1,2-dioxoethyl)-2-ethyl-1-(phenylmethyl)-1H-indol-5-yl]oxy]butanoic acid, or a mixture of (A) through (O).

3. A method for treatment of a human currently afflicted with chronic bronchitis or previously afflicted with chronic bronchitis, said method comprising administering to said human in need of such treatment a therapeutically effective amount of a 1H-indole-3-glyoxylamide compound selected from the group consisting of compounds represented by the formulae:

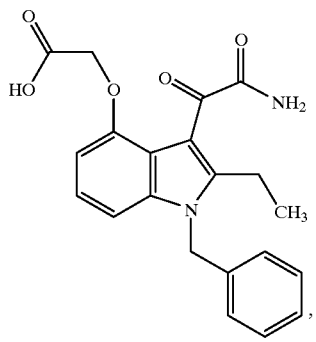
(Va)

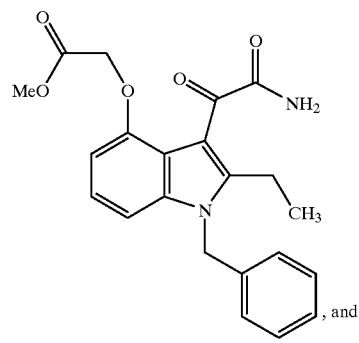
(Vb)

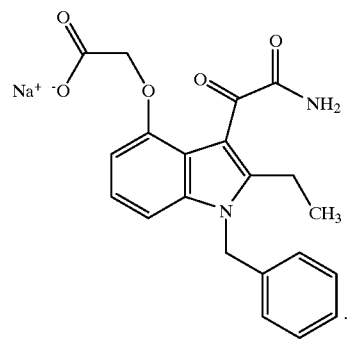
(Vc)

4. The method of claim 1 wherein treatment is of a human currently afflicted with chronic bronchitis, and the therapeutically effective amount is an amount which reduces excessive tracheobronchial mucus production.

5. The method of claim 1 wherein the composition is administered intravenously.

6. The method of claim 1 wherein the compound is administered orally.

7. The method of claim 1 wherein treatment is of a mammal previously afflicted with an chronic bronchitis and the compound is administered in an amount of from 0.01 mg/kg/day to 100 mg/kg/day.

8. The method of claim 1 wherein the therapeutically effective amount of the compound is in the form of a pharmaceutical formulation comprising the compound and a suitable carrier or excipient therefor.

* * * * *